| United States Patent [19] | [11] | 4,451,647 |
|---|---|---|
| Allcock et al. | [45] | May 29, 1984 |

[54] HEPARINIZED POLYORGANOPHOSPHAZENES

[75] Inventors: Harry R. Allcock; Thomas X. Neenan, both of State College, Pa.

[73] Assignee: Research Corporation, New York, N.Y.

[21] Appl. No.: 390,344

[22] Filed: Jun. 21, 1982

[51] Int. Cl.$^3$ .................... A61K 31/725; C08B 37/10
[52] U.S. Cl. ...................................... 536/21; 424/183; 536/117
[58] Field of Search ........................ 536/21, 119, 117

[56] References Cited

U.S. PATENT DOCUMENTS 2,623,001 12/1952 Sylven et al. ........................ 536/21
4,119,774 10/1978 Andersson et al. .................... 536/21
4,239,754 12/1980 Sache et al. ............................ 536/21

*Primary Examiner*—Johnnie R. Brown
*Attorney, Agent, or Firm*—Scully, Scott, Murphy & Presser

[57] ABSTRACT

A polyphosphazene-bound heparin complex comprising a polymeric phosphozine backbone, a quaternary ammonium ion covalently attached to the backbone through a bivalent organic radical attached at one end to the nitrogen atoms of the ion and at the other end to a phosphorus atoms of the backbone, and heparin ionically bound to said quaternary ammonium ion is disclosed along with methods for preparing such complexes.

24 Claims, No Drawings

HEPARINIZED POLYORGANOPHOSPHAZENES

The invention described herein was made in the course of work under a grant from the National Institutes of Health.

BACKGROUND OF THE INVENTION

1. Field of the Invention

This invention relates to an antithrombogenic polymer surface or soluble complex and more particularly to polymeric organophosphazenes which have quarternary ammonium ions in their side chains through which heparin is attached to the polymer backbone.

2. Description of the Prior Art

In recent years a wide variety of materials have been developed for use in direct contact with blood, either temporarily conducting the blood outside the body or in substituting artificial materials for natural materials inside the body. These materials are used, for example, as vascular catheters, cannulas, artificial kidneys, artificial heart-lungs, extra-corporeal circuits for auxiliary circulating devices, A-V shunts, vascular prostheses, artificial heart valves, temporary blood by-pass tubes, and film-like or hollow filament-like dialysis membranes.

Conventional materials which make direct contact with blood have been made from glass, metals, plastics such as soft vinyl chloride resins and silicon resins, graphite, and rubbers such as natural rubber. However, upon contact of such materials with blood, the blood easily coagulates and forms a thrombus on the surface of the material. Even highly inert materials such as polytetrafluoroethylene are likewise known to cause thrombi. The thrombus formed on the artificial surface may stop blood flow in a narrow passageway or may detach from the surface and move with the blood current to cause complications such as cerebral thrombosis, myocardial infarction, or pulmonary thrombosis. Accordingly, it has been common practice when using these biomedical materials to attempt to reduce thrombus formation by systemically administering an antithrombotic agent such as a preparation of heparin, cumarine or sodium citrate to reduce the tendency toward clotting. Unfortunately, systemic administration of these materials has a tendency of causing bleeding in other parts of the individual receiving the treatment.

More recently, artificial surfaces have been treated with heparin so that the heparin is concentrated at the thrombogenic surface rather than being distributed throughout the system as a whole. Several methods have evolved for attaching heparin to various solid surfaces. Since heparin is a sulfated mucopolysaccharide that tends to be negatively charged in physiological solutions, positively charged surfactants which interact with solid surfaces by nonpolar interactions and with the heparin molecule by ionic bonding have been used with previously known inert materials such as graphite; see for example Whiffen et al, Proc. Soc. Exp. Biol. Med., 116, 314 (1964). Other methods, such as covalently binding heparin itself to the surface of a biomedical material have also been proposed; see for example, U.S. Pat. No. 4,331,697 to Kudo et al.

Investigators have recently proposed using polyorganophosphazenes in the manufacture of devices for use in contact with blood such as those previously described. These compounds are polymers with an inorganic backbone normally containing organic sidegroups as shown in the following formula:

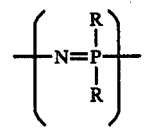

where R is an organic radical. Other drugs have previously been attached to polyphosphazenes. For example, the use of water-soluble polyorganophosphazenes as carriers for coordinatively bonded platinum-containing anti-cancer drugs is disclosed in Allen et al, J. Am. Chem. Soc., 99, 3987 (1977) and Allcock et al, ibid, 3984 (1977). Likewise, U.S. Pat. No. 4,239,755 to Allcock et al discloses a medicament comprising steroidal cyclotriphosphazenes. Polyphosphazenes in contact with blood would benefit from the association of heparin with their surfaces but no method of attachment has previously been proposed or developed.

The chemistry of polyphosphazene polymers, although not established to the extent known for organic polymers, is becoming better known. A recent review in this area indicative of the known chemistry of these macromolecules is Allcock, "High Polymeric Organophosphazenes," Contemporary Topics in Polymer Science, 3, 55 (1979) which is herein incorporated by reference.

However, none of these references disclose or suggest the preparation of heparin attached to a polyorganophosphazene and the need for such substances still exists.

SUMMARY OF THE INVENTION

Accordingly, it is an object of the present invention to provide a heparinized polyorganophosphazene of stable structure.

It is a further object of this invention to provide a method of attaching heparin to a polyorganophosphazene which can be applied to many different types of organic side-groups present in these molecules.

These and other objects of the invention as will hereinafter become more readily apparent have been accomplished by providing a polyphosphazene-bound heparin complex comprising a polymeric phosphazene backbone, a quaternary ammonium ion covalently attached to said backbone through a divalent organic radical attached at one end to the nitrogen atom of said ion and at the other end to a phosphorus atom of said phosphazene backbone, and heparin ionically bound to said quaternary ammonium ion.

DESCRIPTION OF THE PREFERRED EMBODIMENTS

The present invention arose with the discovery that heparin could be attached to an organophosphazene polymer without disrupting the polymer backbone by using a quaternary ammonium ion covalently attached to the backbone to attract the negatively charged heparin molecule. Although quaternary ammonium ions have been used previously to attract heparin to other polymer surfaces, heparin had not previously been attached to a polymer having an inorganic backbone. Since various metal ions are attracted to the inorganic backbone, it was not known whether associating negatively-charged heparin with the surface of a polyorganophosphazene polymer would produce a stable antithrombogenic complex.

The key to the synthesis of poly(organophosphazenes) is the use of a preformed, linear, high polymeric halogenophosphazene as a highly reactive intermediate for substitution reactions. A few organic polymers are prepared by the modification of preformed macromolecules (for instance, the formation of poly(vinyl alcohol) from poly(vinyl acetate), or the chloromethylation of polystyrene), but this method of synthesis cannot be applied generally because of the low reactivity of most organic polymers and the well-known problems that result from chain-coiling in solution or from the deactivation induced by charge generation on nearby repeating units. This modification method, however, forms the main synthetic route to the polyorganophosphazenes.

The overall synthesis routes for poly(organophosphazenes) are shown in Scheme 1.

crosslinks rapidly. The mechanism of this crosslinking process is still not fully understood, although traces of water will accelerate the process, possibly by yielding P-O-P bridging links.

The formation of the uncrosslinked polydichlorophosphazene has been reported in various references and is not considered to be part of the present invention. This synthesis and the synthesis of various polymers therefrom, such as VI-IX, have been reported in, for example, Allcock and Kugel, *J. Am. Chem. Soc.*, 87, 4216 (1965); Allcock et al, *Inorg. Chem.*, 5, 1709 (1966); and Allcock and Kugel, *Inorg. Chem.*, 5, 1716 (1966), all of which are herein incorporated by reference.

In solution, the uncrosslinked form of VI is a highly reactive species. It reacts rapidly with alkoxides, amines, and some organometallic reagents to yield polymers, such as XII–X.

Investigators in the laboratories of the present inventors have recently developed a modification to this

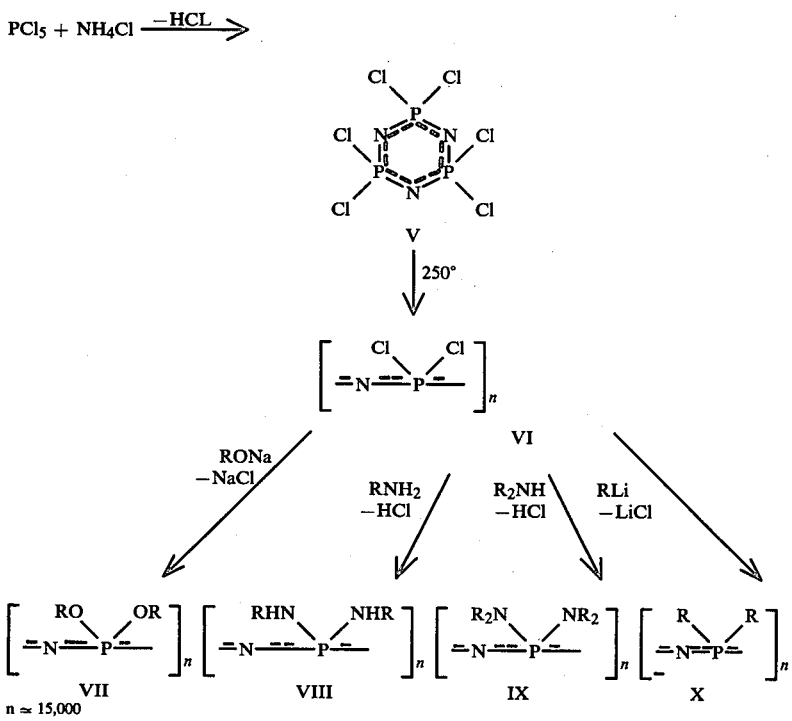

The formation of hexachlorocyclotriphosphazene (V) from phosphorus pentachloride and ammonium chloride or ammonia has been known since the work of Liebig and Wohler in 1834. Similarly, the thermal polymerization of V to a rubbery, crosslinked form of polydichlorophosphazene (VI) was reported by Stokes as early as 1897. However, for over 70 years this polymer was viewed merely as a laboratory curiosity because it is hydrolytically unstable in the atmosphere and is insoluble in all solvents. However, it has since been shown that the polymerization of V to VI is a two-step reaction. During the initial stages of the polymerization (up to ~70–75% conversion of V to VI) an uncrosslinked form of VI is formed. This polymer is soluble in a number of organic solvents, such as benzene, toluene, or tetrahydrofuran. Beyond this stage, the polymer general synthesis route, specifically for the purpose of preparing polymers of structure, X. Polydichlorophosphazene (VI) reacts with organometallic species such as Grignard or organolithium reagents by two different reaction pathways—one favorable and one distinctly unfavorable. These two reactions are alkylation or arylation (XII) on the one hand, the chain-cleavage (XIII) on the other.

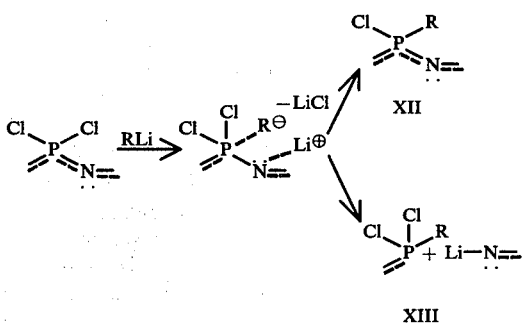

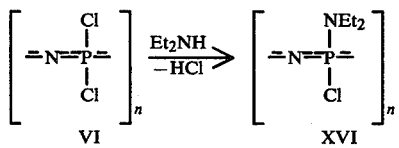

The reactions of amines with poly(dihalophosphazenes) are, in general, more sensitive to mechanistic restrictions than are the substitutions by alkoxides or aryloxides. For example, diethylamine replaces only one chlorine per phosphorus in VI to yield polymers of structure, XVI.

Because the chain cleavage reaction is presumably favored by a high electron-density in the lone-pair-electron orbital at skeletal nitrogen, the inventors have used the more electronegative fluorine atoms in poly(difluorophosphazene) to favor halogen substitution at the expense of chain cleavage. Poly(difluorophosphazene) (XV) can be prepared by the high pressure, high temperature polymerization of hexafluorocyclotriphosphazene (XIV). Once again this is a two-step process. In the first step the reaction mixture contains only a decreasing amount of XIV and an increasing proportion of uncrosslinked XV. In the second stage, XV crosslinks, often when the conversion of XIV to polymer has arisen above ~70%. The reactions of XV with organometallic reagents yield alkylated or arylated high molecular weight polymers, although 100% alkylation or arylation has not yet been achieved without appreciable chain cleavage.

Diphenylamine apparently undergoes no substitution at all. These results reflect the sensitivity of the aminolysis reaction to steric effects and to the nucleophilicity of the amine. Moreover, if poly(difluorophosphazene) (XV) is used as a polymeric intermediate, even primary amines replace only one fluorine per phosphorus, under conditions whre total halogen replacement occurs with polydichlorophosphazene. This effect is ascribed partly to the poor leaving-group ability of fluorine compared to chlorine.

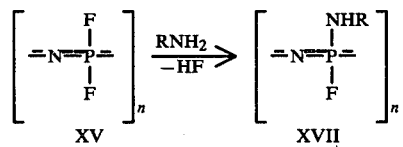

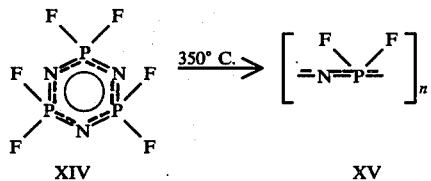

Steric effects are particularly noticeable when bulky nucleophiles such as the steroidal anion shown in XIX are employed. Only one of these molecules can be introduced every three or four repeating units along the polymer chain, and some difficulty is encountered when attempts are made to replace the reamining halogen atoms by less hindered nucleophiles.

In polyphosphazene chemistry an enormous range of different polymers can be prepared by relatively simple techniques from one or two preformed polymeric starting materials. This means that the polymerization problem is a relatively trivial aspect of the synthesis. Different polymers are prepared from the same starting materials merely by modifying the side groups.

This unusual synthetic versatility can, in principle, give rise to an almost unprecedented range of new macromolecules. However, it is important to note that certain restrictions exist with respect to the types and combinations of different substituent groups that can be attached to the polyphosphazene chain.

First, the nucleophilic substitution reactions of poly(-dihalophosphazenes) generally fall into the category of $S_N2$-type replacements. Hence, they are affected by the nucleophilicity and steric characteristics of the attacking nucleophile and and by the leaving-group ability of the halogen. Second, restrictions exist when a prospective nucleophile possesses two or more potential nucleophilic sites. For example, a difunctional reagent (a diamine or diol) could crosslink the chains. Third, as mentioned previously, the possibility exists that the cleavage of phosphorus-nitrogen skeletal bonds might become competitive with phosphorus-halogen bond cleavage. A few examples will illustrate some of the specific restrictions that have been identified.

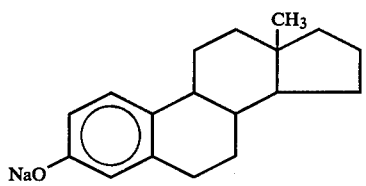

The crosslinking reactions by difunctional reagents are facile processes. Aliphatic or aromatic diamines or the alkoxides generated from diols readily crosslink the chains, either by halogen replacement or, in some cases, by the displacement of organic groups already present. Even ammonia or methylamine can function as cross-linkage agents. However, methylamine does not cross-link the chains at low temperatures, and ethylamine and higher alkyl or primary amines function exclusively as mono- rather than di-nucleophiles.

Perhaps the most serious restriction to the diversification of polyphosphazene structures is found in the tendency of many reagents to induce chain cleavage. The role of organometallic reagents in chain cleavage has already been mentioned. However, carboxylic acids and their alkali metal salts are particularly effective chain-cleavage agents. The mechanisms of these cleavage reactions are only partly understood. Nevertheless, this reaction pathway precludes the use of many biologically active agents as substituent groups unless special care is taken in attaching such radicals to the backbone.

The chemical characteristics of poly(organophosphazenes) can be understood in terms of two factors—the nature of the backbone and the structure of the side group. The chemistry of the backbone is dominated by the presence of the lone-pair electrons on the skeletal nitrogen atoms. The basicity of these nitrogen atoms facilitates protonation, coordination to metals, or hydrogen bonding to water or other protice solvents. For example, the polymer [NP(NHCH$_3$)$_2$]$_n$ forms acid-base "salts" with hydrohalides, functions as a polymeric ligand for transition metals such as platinum, and at the same time is soluble in water or alcohols.

An equally powerful influence on the chemical properties is exerted by the side group structure—sometimes in opposition to the skeletal influence. For example, although the CH$_3$NH— side group confers water-solubility on the polymer, fluorinated side groups, such as CF$_3$CH$_2$O— or CF$_3$CF$_2$CH$_2$O—, give rise to hydrophobicity and water-insolubility. However, these latter side groups provide solubility in ketones or fluorocarbons. The phenoxy group imparts solubility in hot, aromatic hydrocarbons, but insolubility in nearly all other media. Thus the hydrophobicity or hydrophilicity of a polymer can be varied over a wide range by a choice of suitable side groups.

The hydrolytic stability of a polyphosphazene is markedly dependent on the type of side group. Nearly all poly(organophosphazenes) are stable to aqueous media, but the most hydrophobic species are remarkably resistant to hydrolytic degradation. The polymers [NP(OCH$_2$CF$_3$)$_2$]$_n$ and [NP(OC$_6$H$_5$)$_2$]$_n$, are unaffected after years of immersion in strong aqueous sodium hydroxide solution. However, a limited number of side groups are hydrolytic destabilizing groups. For example, polymers that possess —NH$_2$ or —NHCH$_2$COOR groups hydrolyze slowly with moisture.

Polymers according to the present invention may be synthesized as cyclic trimers using hexachlorocyclotriphosphazene, (NPCl$_2$)$_3$, as the starting material, or as linear polymers using polydichlorophosphazene, (NPCl$_2$)$_n$, as the starting material. The exact synthetic method will vary with the structure of the polymer being synthesized but will typically consist of two basic steps: reaction of the intermediate polyhalophosphazene with a molecule that will form the linking group either preceeding or followed by replacement of the remaining halogens with the inactive side groups.

Polymers may be synthesized containing only active side groups (i.e., side groups actively engaged in binding heparin through a quaternary ammonium ion) if desired, but it is preferred to synthesize mixed polymers for ease of control of the physical properties of the polymers. Inactive side groups (i.e., those not having quaternary ammonium ion functional groups) can be used to impart water solubility, water insolubility, or biodegradability as was previously discussed. When mixed polymers are synthesized, it is preferred to form the inactive side groups first since these generally contain fewer functional groups that may interfer with later reactions. This is essential if alkyl or aryl groups are attached directly to the phosphorous of the backbone because of the reactive organometallic reagents used to carry out this reaction. In general there are few limitations on the types of functional groups present in possible inactive side groups; the only prohibited functional groups are those in which a hydrogen is attached to a nitrogen, oxygen, or sulfur. Such functional groups can cause crosslinks to form with other polymer chains or cause undesirable chain cleavage if more than one such group is present at the stage of reacting the side-group precursor with the poly(dihalophosphazene). Examples of undesirable functional groups are hydroxyl, carboxylic acid, primary and secondary amino, thiol, and sulfonic acid groups. However, —NH$_2$ attached to the phosphorous of the backbone is acceptable. Preferred precursors of inactive side groups have the formula HQJ were Q represents —NR— (R is hydrogen or methyl), —O—, or a covalent bond and J represents

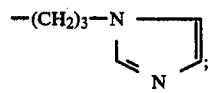

L, where L represents H, a C$_1$-C$_{12}$ alkyl group, or a C$_2$-C$_{12}$ alkyl group substituted by a halogen atoms or —CN or interrupted by a divalent organic functional group of the formula —O—, —COO—, —CONR$^1$, —R$^1$C=CR$^1$—, —C=C—,

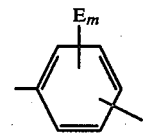

or —CO—, where each R$^1$ independently represents hydrogen or a C$_1$-C$_4$ alkyl group, m is an integer from 0 to 4, and each E independently represents a halogen atom, —NO$_2$, —CN, or R$^1$; or M, where M represents an aryl radical of the formula

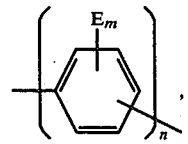

where n is 1 or 2, or

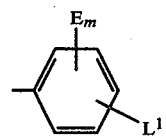

where L$^1$ is —CH$_3$ or L.

The substituents or divalent organic functional groups listed for the C$_1$-C$_{12}$ alkyl groups may independently appear more than once or more than one such substituent or functional group may be present.

Preferred inactive side groups have —NH— or —O— for Q and only halogen atoms or one or two divalent functional groups present in the remainder of the alkyl or aryl side group. Most preferred inactive side groups are —N(CH$_3$)$_2$,

where R² is the side chain of a naturally occuring amino acid,

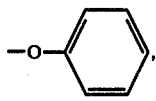

—OCH₂CF₃ and other fluorinated C₂–C₄ alkoxyl groups,

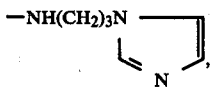

and —NH₂. Those inactive side groups (or later discussed linking groups) that can be prepared from commercially available reagents are especially preferred.

Replacement of chlorine atoms in the backbone of the polyhalophosphazene is carried out in an aprotic organic solvent, preferably an aromatic hydrocarbon such as toluene, by reacting the side group percurser HQJ; its salt GQJ, where G is an alkali metal ion; or the organometallic reagent UJ (where Q is to be a covalent covert bond), where U is a metal ion, with the polyhalophosphazene. The ratio of inactive to active side groups is easily controlled by controlling the mole ratio of percursor HQJ to replaceable halogen atoms. Suitable ratios include from 100:1 to 1:10. Preferred are ratios of 10:1 to 1:2 with about 3:1 being most preferred.

A trialkylamine may be used as a catalyst when the reaction is carried out with HQJ. Triethylamine is preferred.

The polyorganohalophosphazene intermediate is generally not isolated but is reacted with the small molecule that will form the linking group.

The divalent organic radical connecting the nitrogen of the quaternary ammonium ion to a phosphorus of the polymer backbone merely acts as a bridging group. Accordingly, its own internal structure is not critical, although there should be no positive or negatively charged ions present in this linking group which might interfere with the bonding of the quaternary ammonium ion to the heparin molecule. Suitable divalent organic radicals which may serve as the linking group include radicals of the formula —AL— or —AM—, wherein A represents —O— or —NH—; L represents a divalent C₂–C₁₂ alkyl group or a divalent C₂–C₁₂ alkyl group substituted by a halogen atom or —CN or interrupted by a divalent organic functional group of the formula —O—, —COO—, —CONR—, —RC=CR—, —C≡C—,

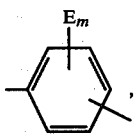

or —CO—, where each R independently represent hydrogen or a C₁–C₄ alkyl group, n is an integer from 0 to 4, and each E independently represents a halogen atoms, —NO₂, —CN, or —R; and M represents a divalent aryl radical of the formula

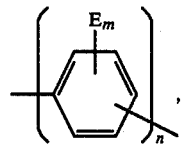

where n is 1 or 2, or $$\underset{L^1-}{\overset{E_m}{\diagdown\!\!\diagup}}$$

where L¹ is L or —CH₂—, and A is directly bonded to a phosphorous of said backbone.

Preferred linking groups are derived from alkoxy, alkylamino, phenoxy, or phenylamino radicals since these may easily be attached to the phosphazene backbone by the chemistry previously discussed. When phenoxy and phenylamino radicals are used, it is preferred that they contain an alkyl group attached to the benzene ring. This facilitates the introduction of the quaternary ammonium ion into the polyorganophosphazene structure. Although there are no limitations on the introduction of the quaternary ammonium ion other than those imposed by other functional groups that may be present, a preferred method involves free radical halogenation of an alkyl side-chain of a polyorganophosphazene as a first step. Free radical halogenation may be carried out by any method which does not result in cleavage of the polymer backbone and does result in halogenation of alkyl groups present in side chains. The location of halogenation will naturally be controlled by the usual steric and thermodynamic factors. Halogenation in locations that can stabilize the initially formed free radicals will occur preferentially, for example, at benzylic carbon atoms. Random halogenation is likely to occur and causes no problems. Halogenation may be carried out in any nonpolar organic solvent which is not halogenated under the reaction conditions used. Carbon tetrachloride (CCl₄) is preferred. Molecular halogen and light or heat may be used but a halogen radical donor, such as an N-halosuccinimide, is preferred. Chlorine and bromine are the preferred halogens with bromine being most preferred.

The amount of halogen introduced controls the relative number of quaternary ammonium groups present in the final product.

A preferred halogenation sequence comprises dissolving the polyorganophosphazene having alkyl carbons in the side chains in CCl₄ followed by addition of N-bromosuccinimide and a free radical initiator such as benzoyl peroxide.

The resulting intermediate, containing alkyl halide functional groups is then converted to a quaternary ammonium salt by standard technique. Typically a trialkylamine, preferably having 1 to 4 carbon atoms per alkyl group, is added in excess to a solution of the polyorganophosphazene intermediate which contains the alkyl halide functional groups in an organic solvent. The resulting quaternary ammonium salt precipitates from solution as it is formed.

Many other methods exist for introducing quaternary ammonium ions in organic side chains. For example, a tertiary amine may be present in the side group when it is initially attached to the phosphazene backbone. This amine could be alkylated, for example with methyl iodide, to form a quaternary amine. Typical organic side groups of this type could be formed from, for example, p-(dimethylamino)phenol or 6-(dimethylamino)-hexanol. Various functional groups present in side chains may also be converted to amines, for example nitro groups by reduction, carbonyl groups by reductive amination, nitriles by reduction, and so forth. The resulting amines are then converted to quaternary ammonium ions as previously described. Suitable techniques of organic chemistry are well known and are described in various standard texts, such as, for example, *Preparative Organic Chemistry*, Hilgetag et al. eds., John Wiley & Sons, New York, 1972, which is herein incorporated by reference.

It is not necessary for all the organic side groups in a polyorganophosphazene of this invention to contain a quaternary ammonium ion. Indeed, this is not the preferred embodiment. It is preferred to have additional organic side groups present of the types previously discussed which may impart water solubility, biodegradability, or biochemical inertness to the polymer as may be desired. This invention contemplates making slight modifications in polyorganophosphazenes which give them the *additional* property of having heparin attached to the molecule rather than causing any major change to their chemical and physical properties as imparted by the organic side groups present in the molecules. As few as one positively charged side group per 100 is believed to be sufficient to attract heparin to the polymer surface, although a 1 to 4 ratio is most preferred. Thus, polyorganophosphazenes of many different properties may be used to attract and hold heparin molecules. Suitable organic side groups include those of the formula —QJ where Q represents —NR$^1$ where R represents hydrogen or methyl, —O—, or a covalent bond and J represents L$^1$H, MH or

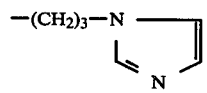

where L$^1$ and M were previously defined. Different organic side groups are permitted in the same molecule.

Several techniques exist for obtaining polyorganophosphazenes having different side groups in the same molecule. This may typically be accomplished by a two-step replacement of the chlorine atoms of a polydichlorophosphazene. Consider, for example, a heparanized phosphazene having 80% of its side groups being —OCH$_2$CF$_3$ and the remaining 20% being

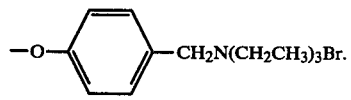

An initial reaction of polydichlorophosphazene with HOCH$_2$CF$_3$ and a base catalyst (or directly with the alkoxide of this alcohol) produces an intermediate polymer having both —OCH$_2$CF$_3$ and —Cl groups attached to phosphorous atoms of the phosphazene backbone if less than an equivalent of the side group precursor is added. The ratio is controlled by controlling the mole ratio of alkoxide added to replacable chlorine atoms.

The intermediate polymer is typically reacted, without being isolated, with a second molecule which introduces the second side chain or its precursor. Here the alkoxides of

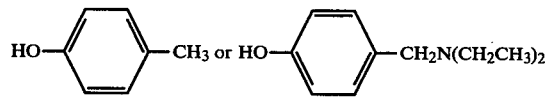

could be used, followed by conversions to the final quaternary ammonium ion by the methods previously discussed.

Water soluble heparin complexes may be prepared by using organic side groups such as C$_1$–C$_4$ alkyl and dialkylamines or C$_1$–C$_4$ esters of naturally occurring amino acids. The latter, along with

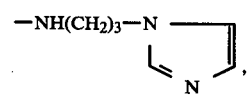

impart hydrolizability to the polymeric complex. Heparin complexes which include these groups may be prepared as injectable solutions for anticoagulation therapy. A detailed discussion of hydrolizable side groups is given in Allcock et al, *Inorg. Chem.*, 21, 515 (1982) which is herein incorporated by reference.

The soluble compounds of this invention can be employed in mixture with conventional excipients, i.e. pharmaceutically acceptable organic or inorganic carrier substances suitable for parenteral application which do not deleteriously react with the active compounds. Suitable pharmaceutically acceptable carriers include but are not limited to water, salt solutions, alcohols, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring and/or aromatic substances and the like which do not deleteriously react with the active compounds.

For parenteral application, particularly suitable are solutions, preferably oil or aqueous solutions, as well as suspension and emulsion. Injections, particularly intravenous injections, are preferred for parenteral administrations. Methods of administering any soluble heparin complex of this invention to a human or animal, particularly a domesticated animal, by any of the means and methods disclosed herein in any amount effective to produce an antithrombogenic effect are also considered to be part of the present invention.

Water insoluble heparin complexes may be used in preparing solid devices which contact blood, such as vascular prostheses or extra-corporeal blood circuits. A preferred embodiment for such devices comprises initially forming the device from a stable polymer having no quaternary ammonium ions in the side chains, and then introducing such ions only at the surface of the solid polymer. A preferred side group is

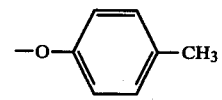

which is hydrolytically stable and can easily be brominated on the methyl group. Other side groups could be present in the same molecule,

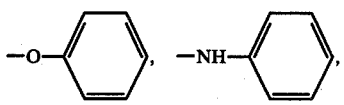

and fluorinated $C_2$–$C_4$ alkyl groups being preferred.

Heparin is associated with the polymer having quaternary ammonium groups by contacting the shaped article or soluble polymer with an aqueous solution of heparin. Commercially available heparin (sodium salt) is dissolved in water to prepare the heparin solution. The contacting time is at least 10 seconds, preferably 30 seconds to 30 hours, more preferably 1 minute to 5 hours. The temperature at which the contacting is carried out is not more than 100° C., preferably not more than 50° C., especially preferably at room temperature.

Examples of the biomedical material which is to be made antithrombotic by the novel heparin derivative of this invention include shaped articles such as catheters, blood bags, blood circuits, A-V shunts for artificial kidneys, dialysis membranes for artificial kidneys and tubes and pumping chambers for blood pumps. It is also possible to impart antithrombotic activity to precursors of these shaped articles, for example films or hollow articles.

Having now generally described this invention, the same will be better understood by reference to certain specific examples, which are included herein for purposes of illustration only and are not intended to be limiting of the invention or any embodiment thereof, unless specified.

EXAMPLE 1

Synthesis of phosphazene trimer-bound heparin

Tetrahydrofuran (THF) (Fisher) used in this and the following reactions was distilled from sodium benzophenone ketal. Carbon tetrachloride (Fisher) was distilled from magnesium sulfate. p-Cresol and N-bromosuccinimide were obtained from Aldrich. Sodium heparin (159 USP K units/mg anhydrous) was obtained from Sigma. All reactions were carried out under an atmosphere of dry nitrogen. A reaction scheme showing the reactions of Examples 1 and 2 follows Example 2.

Compounds 3 (2 g, 0.0026 mol) was dissolved in degassed, dry $CCl_4$ (100 mL) under an atmosphere of dry nitrogen. N-Bromosuccinimide (3 g, 0.0169 mol) was added, followed by benzoyl peroxide (0.2 g). The solution was heated rapidly to reflux, and heating was continued for 3 h. Cooling, filtration, and removal of solvent from the filtrate at reduced pressure yielded 4 as a crude, pale yellow solid. Recrystallization from n-pentane gave the pure product in ≃90% yield. $^1$H NMR spectrum ($CDCl_3$): 6.9 δ (q), 4.5 1 δ (s), integration 2:1.

Excess dry triethylamine (25 mL) was added to a solution of 4 (1 g, $7.9 \times 10^{-4}$ mol) in THF (25 mL). The solution was stirred rapidly as it was cooled over ice. Within 1 h a copious, off-white precipitate (5) had formed. This was filtered off, washed with THF and n-pentane, and vacuum dried. $^1$H NMR spectrum ($D_2O$) 6.9 δ (q), 4.3 δ (s), 3.16 δ (q), 1.4 δ (t): m.p. >300° C.

A solution of 5 (1 g, $5.32 \times 10^{-4}$ mol) in deionized water (10 mL) was added dropwise to a solution of sodium heparin (2% w/v). Within 15 min an off-white precipitate (6) had formed. This was collected on a fine fritted funnel and was washed with copious amounts of deionized water until the washings gave no further precipitate with Toluidine Blue. Compound 6 the trimer-bound heparin, was then dried at 25° C. under vacuum.

EXAMPLE 2

Synthesis of phosphazene polymer-bound heparin

Polymer 7 was prepared by the reaction of $(NPCl_2)_n$ (2) (13.5 g, 0.116 mol) in dioxane (1000 mL) with sodium p-methylphenoxide, prepared from p-cresol (50.17 g. 0.464 mol) and sodium hydride (22.27 g, 0.464 mol) in dioxane (500 mL). The mixture was stirred at reflux for 96 h and was then cooled and filtered to remove sodium chloride. The filtrate was concentrated on a rotary evaporator, and the concentrate was added dropwise to a large volume of water to precipitate the polymer. The crude product was collected by suction filtration. It was then purified by reprecipitation from THF into water (twice), from THF into ethanol (twice) and from THF into n-pentane (three times). The product (7) was dried in vacuo at 60° C. $^1$H NMR spectrum ($CDCl_3$): 6.6 δ (q), 2.0 δ (s), integration 2:1.

To a solution of 7 (2 g, $7.7 \times 10^{-3}$ mol) in carbon tetrachloride (500 mL) was added N-bromosuccinimide (0.69 g, $3.8 \times 10^{-3}$ mol) and benzoyl peroxide (50 mg). The solution was shielded from light and brought rapidly to reflux temperature. Heating was continued until all of the N-bromosuccinimide had been converted to succinimide (1–3 h). The mixture was cooled, filtered, and the polymer was precipitated into n-pentane. Three further precipitations from THF into n-pentane and drying in vacuo yielded 8 (85%). The bromine content in 8 was deduced to be 12.4% on the basis of elemental analysis and $^1$H NMR spectroscopy.

To a solution of 8 (0.5 g, $8.4 \times 10^{-4}$ mol) in THF was added a molar excess of dry triethylamine. The solution was cooled by means of an ice bath and a flocculent white precipitate of 9 occurred within 1 h. A film of 9 was treated with sodium heparin (2% w/v in deionized water) for 24 h at 25° C. The film was washed with 15×25 mL aliquots of deionized water. A Toluidine Blue test showed the absence of heparin in the wash medium after the fourth washing. The polymer was vacuum dried to give an off-white, translucent, tough film (10) which was used in the subsequent clotting tests.

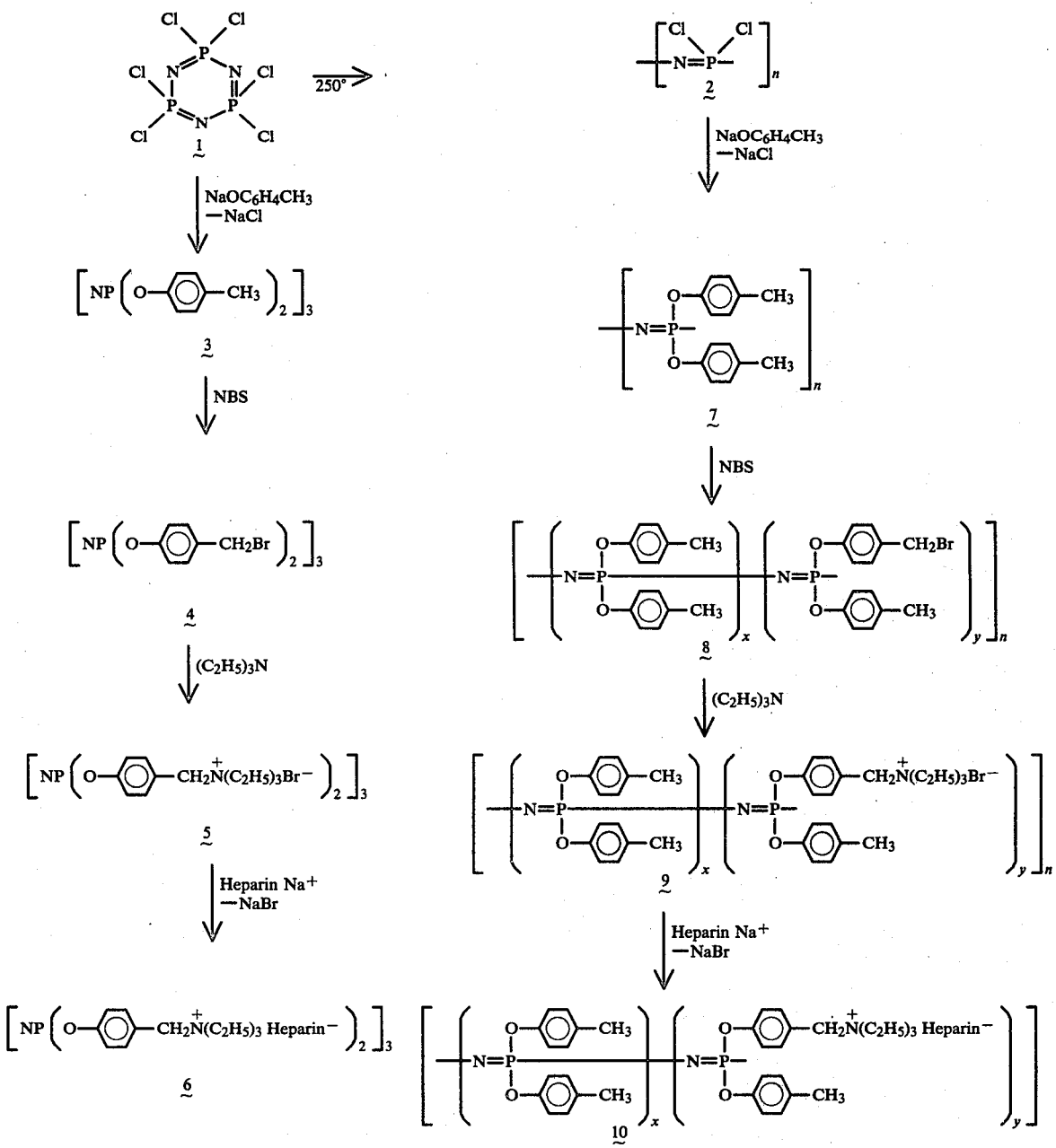

Scheme II

EXAMPLE 3
Blood Clotting Tests

A Lindholm cell was used for the tests. Two polymer samples were examined simultaneously in two matched cells. In each case the surface of the polymer in contact with the blood was approximately 7 cm². The temperature was 25° C. To each cell was added 1 mL of freshly drawn bovine blood. The cells were tilted every 5 min until solid blood clots had formed. Mean clotting times (in brackets) with standard deviations (in parentheses) were as follows: low density polyethylene control [33 min (3.6)]; [NPOC$_6$H$_4$CH$_3$)$_2$]n [12 min (1.8)]; [NP(OC$_6$H$_4$CH$_3$)1.5(OC$_6$H$_4$CH$_2$NEt$_3$.Br)0.5]n[26 min (2.2)]; [NP(OC$_6$H$_4$CH$_3$)1.5(OC$_6$H$_4$CH$_2$NEt$_3$.Heparin)0.5]n [63 min (8.1)]. Some leaching of heparin from the polymer surface is to be expected, and this was indicated by a decrease in clotting time for polymer samples that were reused in the clotting tests.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A polyphosphazene-bound heparin complex, comprising:
   a polymeric phosphazene backbone, a quaternary ammonium ion covalently attached to said backbone through a divalent organic radical attached at one end to the nitrogen atom of said ion and at the other end to a phosphorus atom of said backbone, and heparin ionically bound to said quaternary ammonium ion, wherein said divalent organic radical has the formula —AL— or —AM—, wherein A represents —O— or —NH—, L represents a divalent $C_2$-$C_{12}$ alkyl group or a divalent $C_2$-$C_{12}$ alkyl group substituted by a halogen atom or —CN or interrupted by —O— or a divalent organic functional group of the formula —COO—, —CONR—, —RC=CR—, —C≡C—,

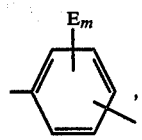

or —CO—, wherein each R independently represents hydrogen or a $C_1$-$C_4$ alkyl group, m is an integer from 0 to 4, and each E independently represents a halogen atom, —$NO_2$, —CN, or —R, and M represents a divalent aryl radical of the formula

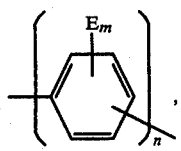

wherein n is 1 or 2, or

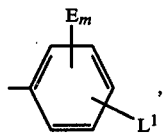

wherein $L^1$ is L or —$CH_2$—, and A is directly bonded to a phosphorous atom of said backbone.

2. The heparin complex of claim 1, wherein said organic radical is an alkoxy radical containing 2 to 12 carbon atoms.

3. The heparin complex of claim 2, wherein said alkoxy radical has the formula —O—($CH_2$—)$_p$ wherein p is from 2 to 12.

4. The heparin complex of claim 3, wherein P is from 2 to 6.

5. The heparin complex of claim 1, wherein said organic radical is a phenoxy radical having the formula

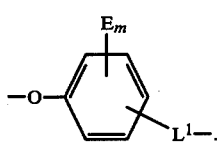

6. The heparin complex of claim 5, wherein said phenoxy radical has the formula

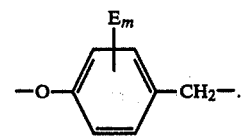

7. The heparin complex of claim 6, wherein m is 0.

8. The heparin complex of claim 1, wherein organic groups of the formula —QJ are attached to phosphorous atoms of said backbone, wherein Q represent —$NR^1$— wherein $R^1$ represents hydrogen or methyl, —O—, or a covalent bond and J represents $L^1$H, MH, or

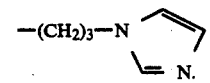

9. The heparin complex of claim 8, wherein the ratio of quaternary ammonium ions to organic groups not containing said ions is from 10:1 to 1:100.

10. The heparin complex of claim 9, wherein said ratio is from 2:1 to 1:10.

11. The heparin complex of claim 9, wherein said ratio is about 1:3.

12. The heparin complex of claim 8, wherein said complex is water soluble.

13. The heparin complex of claim 12, wherein —QJ represents —N($CH_3$)$_2$ or

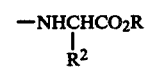

wherein $R^2$ represents hydrogen.

14. The heparin complex of claim 8, wherein said complex is biodegradable.

15. The heparin complex of claim 15, wherein —QJ represents —$NH_2$, or

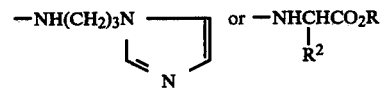

wherein $R^2$ represents H.

16. The heparin complex of claim 8, wherein said complex is biochemically stable.

17. The heparin complex of claim 16, wherein —QJ represents

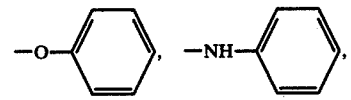

or a fluorinated $C_2$-$C_4$ alkoxyl.

18. The heparin complex of claim 17, wherein —QJ represents —$OCH_2CF_3$.

19. The heparin complex of claim 1, wherein said polymeric phosphazene backbone is a cyclic trimer.

20. The heparin complex of claim 1, wherein said polymeric phosphazene backbone is a linear chain containing from 3 to 30,000

repeating units.

21. The heparin complex of claim 20, wherein said backbone contains from 100 to 20,000 repeating units.

22. The heparin complex of claim 20, wherein said backbone contains about 15,000 repeating units.

23. The heparin complex of claim 12, wherein —QJ represents —N(CH$_3$)$_2$ or

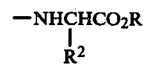

wherein R$^2$ represents a side chain of a naturally occurring amino acid.

24. The heparin complex of claim 14, wherein —QJ represents —NH$_2$, or

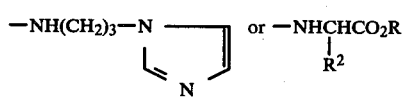

wherein R$^2$ represents a side chain of a naturally occurring amino acid.

* * * * *

UNITED STATES PATENT AND TRADEMARK OFFICE
CERTIFICATE OF CORRECTION

PATENT NO. : 4,451,647
DATED : May 29, 1984
INVENTOR(S) : Harry R. Allcock and Thomas X. Neenan It is certified that error appears in the above-identified patent and that said Letters Patent are hereby corrected as shown below:

Column 13, line 64, "4" should read as --4--.

Column 13, line 68, "4.5 1 δ (s)," should read as --4.5 δ (s),--.

Column 14, line 26, "(2)" should read as --(2)--.

Column 14, line 67, "(10)" should read as --(10)--.

Signed and Sealed this

Ninth Day of April 1985

[SEAL]

Attest:

DONALD J. QUIGG

Attesting Officer     Acting Commissioner of Patents and Trademarks